United States Patent [19]
Bodey

[11] Patent Number: 6,008,002
[45] Date of Patent: *Dec. 28, 1999

[54] IMMUNOMAGNETIC DETECTION AND ISOLATION OF CANCER CELLS

[76] Inventor: Bela Bodey, 15745 Saticoy St., Van Nuys, Calif. 91406

[ * ] Notice: This patent issued on a continued prosecution application filed under 37 CFR 1.53(d), and is subject to the twenty year patent term provisions of 35 U.S.C. 154(a)(2).

[21] Appl. No.: 08/939,483

[22] Filed: Sep. 29, 1997

[51] Int. Cl.[6] .................................................. G01N 33/574
[52] U.S. Cl. ........................ 435/7.23; 435/7.1; 435/7.2; 435/7.5; 435/7.94; 436/64; 436/526
[58] Field of Search ..................... 435/87.1, 7.2, 435/7.23, 7.5, 7.94; 424/138.1, 178.1; 530/387.7, 391.1; 436/526, 64

[56] References Cited

U.S. PATENT DOCUMENTS

| | | |
|---|---|---|
| 5,385,707 | 1/1995 | Miltenyi et al. . |
| 5,541,072 | 7/1996 | Wang et al. . |
| 5,565,365 | 10/1996 | Glass . |
| 5,646,001 | 7/1997 | Terstappen et al. . |

OTHER PUBLICATIONS

Miltenyi Biotec, Auburn, California MACS, Magnetic Cell Sorting With Indirect Micro Beads.
Herlyn et al., Proc. Natl. Acad. Sci USA, Vol. 76, No. 3, pp. 1438–1442, 1979.
Lawless et al. Separation Science and Technology vol. 28(11&12) 1939–1945, 1993.
Durrant et al. Br J Cancer vol. 60 533–537, 1989.

*Primary Examiner*—Laurie Scheiner
*Attorney, Agent, or Firm*—Donald Diamond

[57] ABSTRACT

A composition and method are provided for detecting and isolating antigen associated cancer cells. The composition and method utilize an antigen specific, immunomagnetic composition as the detecting and isolating agent. An illustrative immunomagnetic composition comprises avidin or streptavidin conjugated to paramagnetic beads and further conjugated to antigen specific, biotinylated antibody. A fluidic admixture of the antigen associated cancer cells with the immunomagnetic composition in an affinity column disposed in a magnetic field produces a cancer cell immunomagnetic composition conjugate which is deposited onto the inner wall of the column.

2 Claims, No Drawings

IMMUNOMAGNETIC DETECTION AND ISOLATION OF CANCER CELLS

FIELD OF THE INVENTION

This invention relates to cancer diagnostics and, more particularly, to the use of immunomagnetic compositions and magnetic cell separators for detecting and magnetically isolating antigen associated cancer cells from a specimen solution of such cells.

BACKGROUND OF THE INVENTION

As with all mammalian neoplasms, one of the main factors leading to a better outcome or cure is the earliest possible detection. More specifically, if a colorectal cancer (CC) is detected when it is classified as either Dukes' Class A or B, the patient has a nearly 80% chance of 5-year survival while if the CC is detected when it is classified as a Dukes' C or D, the 5-year survival drops to about 40%. Although adjuvant chemotherapy and local radiotherapy have improved outcomes from CC, no specific public health measure is more likely to benefit such patients than an effective early detection test.

Using analyses based on DNA-loss rates it is estimated that approximately $2 \times 10^{11}$ epithelial cells are shed from the lining of the colon each day. The development of an effective cytological method for the detection of cells shed from tumors of the large bowel has been a topic of major interest for the past half century. The fact remains that after any type of cytological method, the sample is still contaminated to a great extent by stool and bacteria which greatly hamper diagnosis.

Heretofore, numerous methods of limited sensitivity have been employed in an attempt to detect CC as early as possible. The detection of occult blood in stool, for instance, was first held as a very sensitive marker for CC, but only 5% to 10% of the patients in whom occult blood is detected were ultimately diagnosed with CC (Kolata, Science 229:636, 1985; Bader, Diges Dis Sci 31:43s, 1986; Winawer & Miller, Bull WHO 65:105, 1987; Knight et al., JAMA 261:587, 1989). Other methods in common use for the detection of CC, such as sigmoidoscopy, colonoscopy, and contrast enemas are fairly specific and accurate, but due to their invasive and expensive nature have not been suitable for widespread population screening. More recent cytological methods observed the efficacy of increased filtration and isopycnic centrifugation of the lavage or enema samples in Percoll gradients. These studies demonstrated an improvement in the clarity of the final sample, but the loss of cells during the many steps of the procedure makes the method impractical. The increased numbers of false-negative cases which is the result of not being able to see the lost neoplastically transformed cells limits this method greatly.

The complexity and/or invasiveness of the above mentioned methods require well-trained professionals (at least two one to carry out the test and the other to evaluate the results) throughout the procedure, which makes their use in population screening quite expensive. In addition, with these methods screening a single patient may take between six and eight hours. In the case that immunocytochemistry is also applied, the cytologic tests mentioned above are extended four to six hours (and that is if any cancer cells were left after the multiple previous steps of cell isolation and purification).

It would, of course, be advantageous to provide a composition and method for the early detection of colorectal cancer and other cancers which is not invasive, which is not based on multiple centrifugations that may lead to the death of cells crucial in ascertaining the correct diagnosis, and which is extremely specific to the cells under investigation.

OBJECTS

The principal object of this invention is to provide a relatively simple, cost effective method for the identification of neoplastically transformed cells based on immunomagnetic cell separation utilizing neoplastic cell specific monoclonal antibodies conjugated to avidin or streptavidin coated paramagnetic beads as the targeting antibody.

Upon further study of the specification and claims, additional objects and advantages of this invention will become apparent to those skilled in the art.

SUMMARY OF THE INVENTION

In accordance with one aspect of this invention, there is provided an immunomagnetic composition for detecting and magnetically isolating antigen associated cancer cells from a solution thereof disposed within a magnetic field, wherein the composition comprises avidin or streptavidin conjugated to paramagnetic beads and further conjugated to biotinylated monoclonal antibody specific to the antigen associated cancer cells.

In a second aspect of this invention, there is provided a method for detecting and isolating antigen associated cancer cells from a fluid medium which comprises:

(a) admixing said fluid medium with an immunomagnetic composition to produce an admixture wherein said cancer cells conjugate to said immunomagnetic composition, said immunomagnetic composition comprising avidin or streptavidin conjugated to paramagnetic beads and further conjugated to biotinylated monoclonal antibody specific to said antigen associated cancer cells, and (b) subjecting the admixture in an affinity column to an external magnetic force whereby the immunomagnetic composition-cancer cell conjugate is deposited onto the inner wall of the column.

DETAILED DESCRIPTION

The early detection of human neoplasms is of utmost importance and has a very significant effect on the prognosis and outcome of malignant disease. It is well established that colon cancer (CC) patients shed immunocytochemically identifiable, neoplastically transformed cells and that controls have a significantly lower rate of suspicion for transformation cells appearing in their lavage or enema solution or their stool. The use of immunomagnetic cell separation with paramagnetic beads in conjunction with affinity column purification methods, along with the use of specific, primary monoclonal antibodies (MoABs), directed against tumor associated antigens (TAA) on the surface of neoplastically transformed epithelial cells shed from the lining of the colon provides a cell isolation technique from any lavage or enema solution. The cells isolated by this method can then be stained immunocytochemically, without the necessity of the removal of the paramagnetic beads used in the magnetic isolation due to their small diameter, which will allow for facile visualization of transformed colon cells with malignant potential and the identification of their immunophenotype (IP). This early detection method for CC is cost effective and simple and may, therefore, be used for preventative purposes in population screening.

It is apparent that by the substitution of the MOAB being used and the system of the body where the lavage is administered or the cell sample obtained, cancers of other types will also be readily detected using the method described herein. This method is also completely applicable to veterinary medicine, with the employment of species-specific antibodies.

The invention described herein for the early detection of certain cancers can be practiced by the use of Streptavidin MicroBeads complexed with MoABs directed against tumor specific (TS) or TAAs and employed in a magnetic field, column purification method (Miltenyi Biotec Inc., Auburn, Calif. 95603) for the facile isolation of neoplastically transformed cells and the further visualization and characterization of these cells, as to their malignant potential related to the degree of progression of the tumor, by cytospin immunochemistry.

Streptavidin MicroBeads are available from Miltenyi Biotec Inc. as colloidal super-paramagnetic MicroBeads (iron-dextran complex) conjugated to streptavidin. The product is supplied as a suspension containing 0.1% gelatin and 0.05% sodium azide.

In the magnetic cell sorting procedure, as described by Miltenyi Biotec Inc., the biological material of interest (e.g. cells, bacteria or subcellular material) is labelled with biotinylated antibody or other biotinylated ligands/molecules and thereafter magnetically labelled with Streptavidin Micro-Beads whereby the material of interest is separated on a column when the column is placed in a magnetic field.

High gradient magnetic separation (HGMS) of biologicals is reviewed and discussed in several U.S. patents including U.S. Pat. No. 5,385,707 (Miltenyi et al., 1995), U.S. Pat. No. 5,541,072 (Wang et al., 1996) and U.S. Pat. No. 5,646,001 (Terstappen et al., 1997), all of which are incorporated herein by reference. U.S. Pat. No. 5,385,707 discloses a process for preparing superparamagnetic colloidal coated particles for use in HGMS, which process comprises precipitating magnetic iron oxide (from ferric/ferrous ion solution) in colloidal form, treating the colloid with a suitable coating material such as dextran, and thereafter derivatizing (conjugating) the coated magnetic particles to a specificity—conferring moiety such as avidin or biotin.

The use of biotin conjugates (such as biotinylated monoclonal antibodies) and avidin/streptavidin conjugates (such as radioactive streptavidin) for tumor detection, imaging and therapy is disclosed in the prior art. See U.S. Pat. No. 5,482,698 (Griffiths, 1996) and the patents and literature references cited therein.

Iron-dextran complexes are discussed in U.S. Pat. No. 5,624,668 (Lawrence, et al., 1997) including the use of dextrans of various molecular weights as ingredients in the synthesis of magnetic colloids or particles, making reference to U.S. Pat. No. 4,101,435 (Hasegawa, et al.).

The invention described herein combines immunomagnetic separation of CC cells from the lavage and enema solutions or stool samples of patients, using primary anti-TAA specific MOAB and streptavidin conjugated paramagnetic beads for cancer cell separation and purification. The further visualization and IP characterization of the isolated cancer cells by immunocytochemical staining will complete the early detection method for CC cells.

The immunocytochemical localization of cancer cells employing various antibodies is well documented in the medical literature. The method presented here is based on the highly specific binding of MoABs to cells expressing the target antigenic epitope, thereby allowing for the selective enrichment of particular cell populations based on their immunophenotypical characteristics. Solutions or diluted stool samples have been shown to contain viable cells shed from the epithelial lining of the colon. The presence of neoplastically transformed cells among these cells in patients with CC is certain. By using MoABs directed against TAAs present in a large concentration on the surface of CC cells, such as Gastric Mucin Ab-1 (clone 45M1) and Mucin 2 (MUC2) Ab-1 (clone CCP58) (Neomarkers, Inc., Fresno, Calif.), and CA19-9 (clone ZY-C09) (Zymed Laboratories, Inc., San Francisco, Calif.), for conjugating to streptavidin conjugated paramagnetic beads, targeting compositions are obtained which selectively bind and isolate neoplastically transformed cells expressing antigens bound by these MoABs from a solution thereof (such as that derived following oral lavage or enema administration) resulting in the specific retention/isolation of the desired cells.

The applicable method involves the following sequential steps following preparation of the test solutions (derived from the subjects).

(1) 200 µl of the solution of streptavidin conjugated paramagnetic beads are added to a test tube and mixed with 100 microliters of the concentrated (100–200 µl/ml) biotinylated TAA-directed MOAB. Avidin, found in egg whites, has a very high binding affinity for biotin ($10^{-19}$M), which is a B complex vitamin (Griffiths, U.S. Pat. No. 5,482,698; Rosebrough, U.S. Pat. No. 5,326,778; Wilchek, et al., Anal Biochem., 171:1, 1988). Streptavidin, present on the streptavidin conjugated paramagnetic beads mentioned above, is derived from *Streptomyces avidinii*. It is similar to avidin except for the fact that it has lower non-specific binding to tissues by virtue of the fact that it is not glycosylated, and is therefore often used in place of avidin to ensure greater specificity. Both avidin and streptavidin are tetravalent for biotin, allowing amplification of the signal at the site of the binding. The term "antibody" as in "monoclonal antibody (MOAB)" or "polyclonal antibody" is meant generally to include immunoglobulins that specifically bind to antigens present on cell surfaces forming immune complexes. MoABs and polyclonal antibodies are equally suitable for use in the present invention as long as they represent antibodies targeted to antigens specific for or highly associated with a particular malignancy. The antibodies are affinity purified (to at least 95% homogeneity for MoABs) and thoroughly characterized prior to use in the present invention. Several different antibodies are described above and below which can be utilized in the immunomagnetic isolation of transformed cells, but these are simply representative antibodies and are not presented in a limiting sense. Any novel antibodies which may be discovered in the future which can be utilized in the basic method described herein to facilitate the isolation of neoplastically transformed cells from solution (e.g. lavage, enema) are deemed as much a part of this invention as the ones identified herein.

(2) The solution of streptavidin conjugated paramagnetic beads indirectly coated with a TAA-specific MOAB, directed against antigens present in large concentration on neoplastically transformed colonic epithelial cells and in minimal amounts on normal cells as prepared in Step 1, is then added to the enema or lavage solution (up to 500 ml), mixed and allowed to incubate for 45 minutes at room temperature.

(3) The solution after the incubation is then divided into several fractions in glass affinity columns (number and volume depending on the volume of the initial solution, but each not to exceed 50 ml), and the affinity columns are then placed in a U-shaped magnet for separation of the cells associated with the antibody on the paramagnetic beads. These cells are attracted to and deposited on the inside wall of the glass affinity column and the solution in the middle of the column containing non-specific cellular and non-cellular contaminants is withdrawn using a pipette.

(4) The remaining solution of cells is resuspended in either PBS, TBS, or RPMI-1640 medium. Thus, a pure solution of only the cells expressing the particular colorectal cancer associated antigens are retained, and due to the minimal size of the paramagnetic beads, simple histochemical or, if desired, immunocytochemical staining, can be carried out just as soon as slides are prepared from this solution (it is not necessary to remove the paramagnetic beads).

(5) The preparation of cytospins is done by spinning cells from the magnetically enriched fraction onto a slide using a cytocentrifuge (e.g. Cytospin 3, Shandon-Lipshaw, Pittsburgh, Pennsylvania). The slides can now be stained by simple histological methods or by immunocytochemical technique (if desired). For immunostaining, alkaline phosphatase (AP) conjugation to the biotin-streptavidin complex present at the antigen-antibody immunocomplex is done for 20 minutes, followed by washing in PBS (three times for 10 minutes each). The developer, AP Substrate Kit I (Vector Laboratories, Burglingame, California), which contains ASTR with Tris-HCl buffer at pH 8.2, is then added for 25 to 48 minutes to allow formation of the stable product for visualization of the primary antigen-antibody complex (various intensities of red). Filtered hematoxylin solution (Mayer) is then used to counterstain nuclei, followed by dehydration in 95% and 100% ethanol, and clearing in Histo-Clear (National Diagnostics, Manville, N.J.). Mounting is performed with non-aqueous, permanent media (Acrytol/Surgipath Medical Industries, Grayslake, Ill.).

In view of the foregoing description, it is apparent that by changing the MOAB being used and the system of the body where the lavage is administered or the cell sample obtained, cancers of other types will also be readily detected using the method described herein. For example, by the use of samples derived following the administration of bronchoalveolar lavage, and MoABs detecting TAAs associated with different lung carcinoma cells [such as anti-Carcinoembryonic Antigen (CEA) (Neomarkers, Inc.) and anti-MOC-31 (clone M3525) (DAKO, Carpenteria, Calif.) MoABs], a similar procedure exists for the early detection of lung cancer. Additionally, by changing the MOAB employed, cells of any type, including tumor infiltrating leukocytes, containing cytotoxic T lymphocytes (CTL) or natural killer (NK) cells may also be isolated from any such cell suspension. It should also be noted that the procedure described herein is completely applicable to veterinary medicine, with the employment of appropriate species-specific antibodies.

The following examples further illustrate the invention:

EXAMPLE I

The first patient whose lavage sample was tested using the above described method was a male with a diagnosis of adenocarcinoma of the colon. As is the normal procedure prior to resection of the tumor, the large bowel was cleansed by the administration of oral lavage (Colyte). Examination of the solution by the method described herein found a great number of tumor cells (on the order of $10^3$–$10^5$ cells), which were then stained. Upon microscopic inspection, it was confirmed that these were indeed neoplastically transformed cells, in various stages of maturation.

EXAMPLE II

A female patient with a diagnosis of colon adenoacarcinoma was observed. As is the normal procedure prior to resection of the tumor, the large bowel was cleansed by the administration of oral lavage (Colyte). Part of this solution was examined in accordance with the procedure described herein and a great number of tumor cells were found (on the order of $10^3$–$10^5$ cells), which were then stained. Upon microscopic inspection, it was confirmed that these were indeed neoplastically transformed cells, in various stages of maturation.

EXAMPLE III

A female patient with duodenal ulcer was examined as a control to confirm the specificity of the method described herein. The patient was administrated PBS lavage (usually 1.5 L to 2 L). As expected, no malignant cells were detected in the lavage solution that was examined in accordance with the procedure described herein. Slides from the solution that was withdrawn from the column were prepared, following the immunomagnetic step using the two CC antibodies mentioned above and no staining was detected.

EXAMPLE IV

A male patient suffering from chronic gastritis was examined as a control to confirm the specificity of the method described herein. The patient was administered PBS lavage (usually 1.5 L to 2 L). As expected, the immunomagnetic procedure did not detect any malignant cells in the lavage solution. Slides were prepared from the solution that was withdrawn from the column, after the necessary purification and immunocytochemistry step using the two CC antibodies mentioned above, and no staining was detected.

EXAMPLE V

In order to test and re-test the efficacy of the method described herein, a further group of 25 patients (13 male; 12 female) were examined. In every one of these cases the diagnosis was a carcinoma of the colon. All of these patients underwent cleansing of the large bowel prior to resection of the malignancy by the administration of oral lavage (Colyte). A part of each patient's solution was examined by the procedure described herein. It was observed that a significant number of neoplastically transformed cells (on the order of $10^3$–$10^5$ cells) reacted with the TAA-directed MoABs as previously described. Slides were prepared of the cell suspensions being stained. Upon microscopic inspection, it was confirmed that these were indeed cells derived from the malignancy. The control group during these observations included 15 patients (8 male; 7 female) suffering from other gastrointestinal tract ailments (i.e. inflammation, ulcers, etc.). The patients in the control group underwent the same procedure as the study group. In these control patients, no cells bound to the MOAB conjugated paramagnetic beads in the affinity column and thus no cells were retained. Examination of the solution that was withdrawn from the affinity column by the preparation of slides and the staining of the cells using the same MoABs that were in the column further confirmed the absence of neoplastically transformed cells in these patients since there was no staining.

In contrast to prior art procedures, the method described herein is not invasive, is not based on multiple centrifugations which may lead to the death of cells crucial in ascertaining the correct diagnosis and is extremely specific for tumor cells due to the use of MoABs directed against TAAs on the surface of cancer cells.

Neoplastically transformed cells isolated using certain TAA-directed MOAB are easily stained by immunocytochemistry and observed under a microscope. The total time required for the entire procedure including immunocytochemistry is between two and three hours. The presence of cells isolated with a specific MOAB against a TAA has been shown to only occur in cases of cancer for which the appropriate TAA was targeted. For example, gastric cancer cells were not isolated using a MOAB directed against a TAA on colorectal carcinoma cells. The method lends itself to use in large scale population screening due to its simple nature and quick and unequivocal results. The immunostaining of the cell does not require that the MOAB conjugated paramagnetic beads be separated from the cell since they are small enough in size as to not interfere with the binding of the alkaline phosphatase to the streptavidin-biotin complexes. The cell yield is thus maximized since the cells are not subjected to any further stresses. The staining is a very straightforward procedure.

The simplicity of the method allows regular laboratory personnel to carry out the reaction and the results of the tests are very clear: either neoplastically transformed cells are present and can be stained (they stain red) or none are present.

In view of the foregoing descriptions and examples, it will become apparent to those of ordinary skill in the art that equivalent modifications thereof may be made without departing from the spirit and scope of this invention.

That which is claimed is:

1. A cost effective method for widespread population screening for detecting and isolating antigen associated colorectal cancer cells from a lavage or enema fluid medium which comprises:

admixing said lavage or enema fluid medium with an immunomagnetic composition to produce an admixture wherein said antigen associated colorectal cancer cells conjugate to said immunomagnetic composition, said immunomagnetic composition comprising avidin or streptavidin conjugated to colloidal paramagnetic beads and further conjugated to biotinylated antibody specific to said antigen associated cancer cells, said admixing step being free of immunofluorescent composition, subjecting the admixture in an affinity column to an external magnetic force whereby the immunomagnetic composition antigen associated colorectal cancer cell conjugate is deposited on the inner wall of the column, separating said conjugate from said affinity column, and staining and visualizing said conjugate to detect antigen associated colorectal cancer cells, said colloidal paramagnetic beads being of sufficiently small diameter to permit staining and visualization of antigen associated colorectal cancer cells from a conjugate of said cells with said immunomagnetic composition, without removal of said beads from said conjugate, said method excluding the step of cell destroying centrifugation whereby the integrity of the cells to be examined is maintained, and said method being free of enzymatic composition.

2. The method of claim 1 wherein the paramagnetic beads comprise iron-dextran complex.

* * * * *